United States Patent
Kemp et al.

(10) Patent No.: US 10,770,180 B1
(45) Date of Patent: Sep. 8, 2020

(54) PROCESSING CLINICAL NOTES USING RECURRENT NEURAL NETWORKS

(71) Applicant: Google LLC, Mountain View, CA (US)

(72) Inventors: Jonas Beachey Kemp, Sunnyvale, CA (US); Andrew M. Dai, San Francisco, CA (US); Alvin Rishi Rajkomar, San Jose, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 16/712,947

(22) Filed: Dec. 12, 2019

Related U.S. Application Data

(60) Provisional application No. 62/778,833, filed on Dec. 12, 2018.

(51) Int. Cl.
  *G16H 50/20* (2018.01)
  *G06N 3/04* (2006.01)
  *G16H 10/60* (2018.01)
  *G16H 50/30* (2018.01)

(52) U.S. Cl.
  CPC ............ *G16H 50/20* (2018.01); *G06N 3/049* (2013.01); *G16H 10/60* (2018.01); *G16H 50/30* (2018.01)

(58) Field of Classification Search
  CPC ........ G16H 50/20; G16H 50/30; G16H 10/60; G06N 3/049
  See application file for complete search history.

(56) References Cited

U.S. PATENT DOCUMENTS

| | | | |
|---|---|---|---|
| 2014/0207492 A1* | 7/2014 | Farooq | G06Q 10/10 705/3 |
| 2016/0298198 A1* | 10/2016 | Hernando-Monge | A61K 38/212 |
| 2019/0034591 A1* | 1/2019 | Mossin | G06N 3/0445 |
| 2019/0221294 A1* | 7/2019 | Jung | G16H 10/60 |
| 2020/0027567 A1* | 1/2020 | Xie | G16H 10/60 |

OTHER PUBLICATIONS

Abadi et al., "TensorFlow: Large-Scale Machine Learning on Heterogeneous Distributed Systems," arXiv:1603.04467, Mar. 2016, 19 pages.

(Continued)

*Primary Examiner* — Christopher L Gilligan
(74) *Attorney, Agent, or Firm* — Fish & Richardson P.C.

(57) ABSTRACT

Methods, systems, and apparatus, including computer programs encoded on computer storage media, for predicting future patient health using neural networks. One of the methods includes receiving electronic health record data for a patient; generating a respective observation embedding for each of the observations, comprising, for each clinical note: processing the sequence of tokens in the clinical note using a clinical note embedding LSTM to generate a respective token embedding for each of the tokens; and generating the observation embedding for the clinical note from the token embeddings; generating an embedded representation, comprising, for each time window: combining the observation embeddings of observations occurring during the time window to generate a patient record embedding; and processing the embedded representation of the electronic health record data using a prediction recurrent neural network to generate a neural network output that characterizes a future health status of the patient.

20 Claims, 3 Drawing Sheets

(56) References Cited

OTHER PUBLICATIONS

Adebayo et al., "Sanity Checks for Saliency Maps," NIPS, Oct. 2018, 28 pages.
Boag et al., "What's in a Note? Unpacking Predictive Value in Clinical Note Representations," AMIA Summits Transl. Sci. Proc., May 2018, 26-34.
Che et al., "Recurrent Neural Networks for Multivariate Time Series with Missing Values," Scientific Reports, Apr. 2018, 8(6085): 12 pages.
Cheng et al., "Risk Prediction with Electronic Health Records: A Deep Learning Approach," Proceedings of the 2016 SIAM International Conference on Data Mining, Jun. 2016, 9 pages.
Choi et al., "Doctor AI: Predicting Clinical Events via Recurrent Neural Network," MLHC, Sep. 2016, 56:18 pages.
Choi et al., "Using recurrent neural network models for early detection of heart failure onset," J. Am. Med. Inform. Assoc., Feb. 2017, 24(2):361-370.
Chokwijitkul et al., "Identifying Risk Factors for Heart Disease in Electronic Medical Records: A Deep Learning Approach," Proceedings of the BioNLP 2018 Workshop, Jul. 18-27, 2018.
Chung et al., "Hierarchical Multiscale Recurrent Neural Networks," arXiv:1609.01704, Sep. 2016, 15 pages.
Dai et al., "Semi-supervised Sequence Learning," Neural Information Processing Systems, NIPS, Dec. 2015, 9 pages.
Esteban et al., "Predicting Clinical Events by Combining Static and Dynamic Information Using Recurrent Neural Networks," https://arxiv.org/abs/1602.02685, last revised Nov. 2016, 9 pages.
Fries, "Brundlefly at SemEval—2016 Task 12: Recurrent Neural Networks vs. Joint Inference for Clinical Temporal Information Extraction," https://arxiv.org/abs/1606.01433, Jun. 2016, 7 pages.
Gal et al., "A Theoretically Grounded Application of Dropout in Recurrent Neural Networks," NIPS, Dec. 2016, 9 pages.
Gao et al., "Hierarchical attention networks for information extraction from cancer pathology reports," J. Am. Med. Inform. Assoc., Mar. 2018, 25(3):321-330.
Golovin et al., "Google Vizier: A Service for Black-Box Optimization," Proceedings of the 23rd ACM SIGKDD International Conference on Knowledge Discovery and Data Mining, Aug. 2017, 1487-1496.
Hochreiter et al., "Long Short-term Memory," Neural Computation, Nov. 1997, 9:1735-1780.
Hwang et al., "Character-Level Language Modeling with Hierarchical Recurrent Neural Networks," https://arxiv.org/abs/1609.03777v1, last revised Sep. 2016, 9 pages.
Jacobson et al., "Applying deep learning on electronic health records in Swedish to predict healthcare-associated infections," Proceedings of the 15th Workshop on Biomedical Natural Language Processing, Aug. 2016, 191-195.
Jagannatha et al., "Structured prediction models for RNN based sequence labeling in clinical text," Proceedings of the 2016 Conference on Empirical Methods in Natural Language Processing, Nov. 2016, 856-865.
Johnson et al. "MIMIC-III, a freely accessible critical care database," Scientific Data, May 2016, 3:160035, 9 pages.
Johnson et al. "Google's Multilingual Neural Machine Translation System: Enabling Zero-Shot Translation," Transactions of the Association for Computational Linguistics, Oct. 2017, 5:339-351.
Kingma et al., "Adam: A Method for Stochastic Optimization," https://arxiv.org/abs/1412.6980v8, Jul. 2015, 15 pages.
Krueger et al. "Zoneout: Regularizing RNNs by Randomly Preserving Hidden Activations," arXiv:1606.01305v1, Jun. 2016, 10 pages.
Lipton et al., "Learning to Diagnose with LSTM Recurrent Neural Networks," arXiv:1511.03677v1, Nov. 2015, 14 pages.
Lv et al., "Clinical Relation Extraction with Deep Learning," International Journal of Hybrid Information Technology, Jul. 2016, 9(7):12 pages.
Meng et al., "Hierarchical RNN with Static Sentence-Level Attention for Text-Based Speaker Change Detection," Proceedings of the 2017 ACM on Conference on Information and Knowledge Management—CIKM '17, Nov. 2017, 2203-2206.
Miotto et al., "Deep Patient: An Unsupervised Representation to Predict the Future of Patients from the Electronic Health Records," Scientific Reports, May 2016, 6:26094, 10 pages.
Newman-Griffis et al., "Embedding Transfer for Low-Resource Medical Named Entity Recognition: A Case Study on Patient Mobility," Proceedings of the BioNLP 2018 Workshop, Jul. 2018, 11 pages.
Nguyen et al., "Deepr: A Convolutional Net for Medical Records," IEEE Journal of Biomedical and Health Informatics, Jan. 2017, 21(1):22-30.
Nickerson et al., "Deep neural network architectures for forecasting analgesic response," Conf. Proc. IEEE Eng. Med. Biol. Soc., Jul. 2016, 2966-2969.
Pedregosa et al., "Scikit-learn: Machine Learning in Python," Journal of Machine Learning Research, Oct. 2011, 12:2825-2830.
Pham et al., "DeepCare: A Deep Dynamic Memory Model for Predictive Medicine," https://arxiv.org/abs/1602.00357v1, Feb. 2016, 27 pages.
Phan et al., "SeqSleepNet: End-to-End Hierarchical Recurrent Neural Network for Sequence-to-Sequence Automatic Sleep Staging," https://arxiv.org/abs/1809.10932v2, Sep. 2018, 11 pages.
Pollard et al., "MIMIC-III Clinical Database," Sep. 2016, retrieved on Jan. 2, 2020, retrieved from URL <https://physionet.org/content/mimiciii/1.4/>, 10 pages.
Rajkomar et al., "Scalable and accurate deep learning with electronic health records," NPJ Digital Medicine, May 2018, 1:18: 10 pages.
Samonte et al., "ICD-9 Tagging of Clinical Notes Using Topical Word Embedding," Proceedings of the 2018 International Conference on Internet and e-Business—ICIEB '18, Apr. 2018, 118-123.
Sha et al., "Interpretable Predictions of Clinical Outcomes with an Attention-based Recurrent Neural Network," Proceedings of the 8th ACM International Conference on Bioinformatics, Computational Biology, and Health Informatics—ACM-BCB '17, Aug. 2017, 233-240.
Shickel et al., "Deep EHR: A Survey of Recent Advances in Deep Learning Techniques for Electronic Health Record (EHR) Analysis," IEEE Journal of Biomedical and Health Informatics, Sep. 2018, 22(5):1589-1604.
Sundararajan et al., "Axiomatic Attribution for Deep Networks," arXiv:1703.01365v2, Jun. 2017, 11 pages.
Suresh et al. "Clinical Intervention Prediction and Understanding with Deep Neural Networks," MLHC, Nov. 2017, 68:16 pages.
Vani et al., "Grounded Recurrent Neural Networks," arXiv:1705.08557v1, May 2017, 11 pages.
Walsh et al., "The effects of data sources, cohort selection, and outcome definition on a predictive model of risk of thirty-day hospital readmissions," J. Biomed. Inform., Dec. 2014, 52:418-426.
Yang et al. "Hierarchical Attention Networks for Document Classification," Proceedings of the 2016 Conference of the North American Chapter of the Association for Computational Linguistics: Human Language Technologies, Jun. 2016, 1480-1489.
Yu et al., "Video Paragraph Captioning Using Hierarchical Recurrent Neural Networks," https://arxiv.org/abs/1510.07712v2, last revised Apr. 2016, 10 pages.

* cited by examiner

PROCESSING CLINICAL NOTES USING RECURRENT NEURAL NETWORKS

CROSS-REFERENCE TO RELATED APPLICATION

This application claims priority to U.S. Provisional Application No. 62/778,833, filed on Dec. 12, 2018. The disclosure of the prior application is considered part of and is incorporated by reference in the disclosure of this application.

BACKGROUND

This specification relates to processing inputs using a neural network.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system of one or more computers in one or more physical locations that makes predictions that characterize the predicted future health of a patient based on electronic health record data for the patient. In particular, the electronic health data includes clinical notes and, as part of generating the prediction, the system generates an embedding of each clinical note using a clinical note embedding long short-term memory (LSTM) neural network.

Particular embodiments of the subject matter described in this specification can therefore be implemented so as to realize one or more of the following advantages.

Clinical notes provide immense value to clinicians as a summary of a patient's clinical state and are essential to a patient's care. However, while other parts of a patient's record are uniformly coded and easily accessible to predictive models and computer systems (such as billing systems), clinical notes remain inscrutable to automated analysis.

Clinicians can spend significant amounts of time writing clinical notes that contain patient histories, assessment of clinical conditions, and a discussion of recommended therapies. The notes are a critical source of information that is not recorded elsewhere, such as the exact characteristics of a joint exam or diagnoses made from clinical assessment (e.g., alcohol withdrawal). However, these notes are also an imperfect source of information, containing redundancies or importing out-of-date data from the structured portion of the electronic health record (EHR). Automated information extraction from the raw, free text of the notes is difficult due to variance in clinicians' styles of writing. Clinicians may use their own abbreviations, and may organize the note in various different ways. Notes are often not written in standard English, as busy clinicians may use non-standard and inconsistent abbreviations (for example, pt and ptnt for patient) or skip over non-essential words such as adverbs.

For the above reasons, conventional techniques that analyze electronic health record data to make predictions about patient's health have not been able to effectively incorporate clinical notes. In particular, conventional techniques for incorporating clinical notes into predictive models have not proven to be effective in improving the accuracy of the predictions generated by these models. In many conventional predictive models, clinical notes have been ignored outright; those that use notes may simply split them into word-level tokens and use the top N most frequent tokens (or an expert-selected subset of tokens) as independent predictor variables in a model, ignoring many subtleties of language such as conjunctions and negations.

The described techniques, on the other hand, effectively incorporate clinical notes to generate highly-accurate predictions about the patient's future health. In particular, the described systems and techniques scalably and automatically extract relevant information from notes in the context of the entire clinical record by applying a hierarchical recurrent neural network that is able to read variable-length notes sequentially in tandem with other data from the medical record, without assuming any particular layout, medical vocabulary, writing style or language rules in the notes. In particular, a low-level LSTM (or other recurrent neural network) generates embeddings of notes that consider the context of the text in the note, while a higher-level LSTM (or other recurrent neural network) processes the embeddings of the notes along with embeddings of other types of observations to make accurate predictions.

The described approach to modelling clinical notes significantly improves predictive performance over strong commonly-used baselines (a model without clinical notes and one using bags of word embeddings) on multiple tasks, even those requiring extraction of information that are only recorded in notes.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
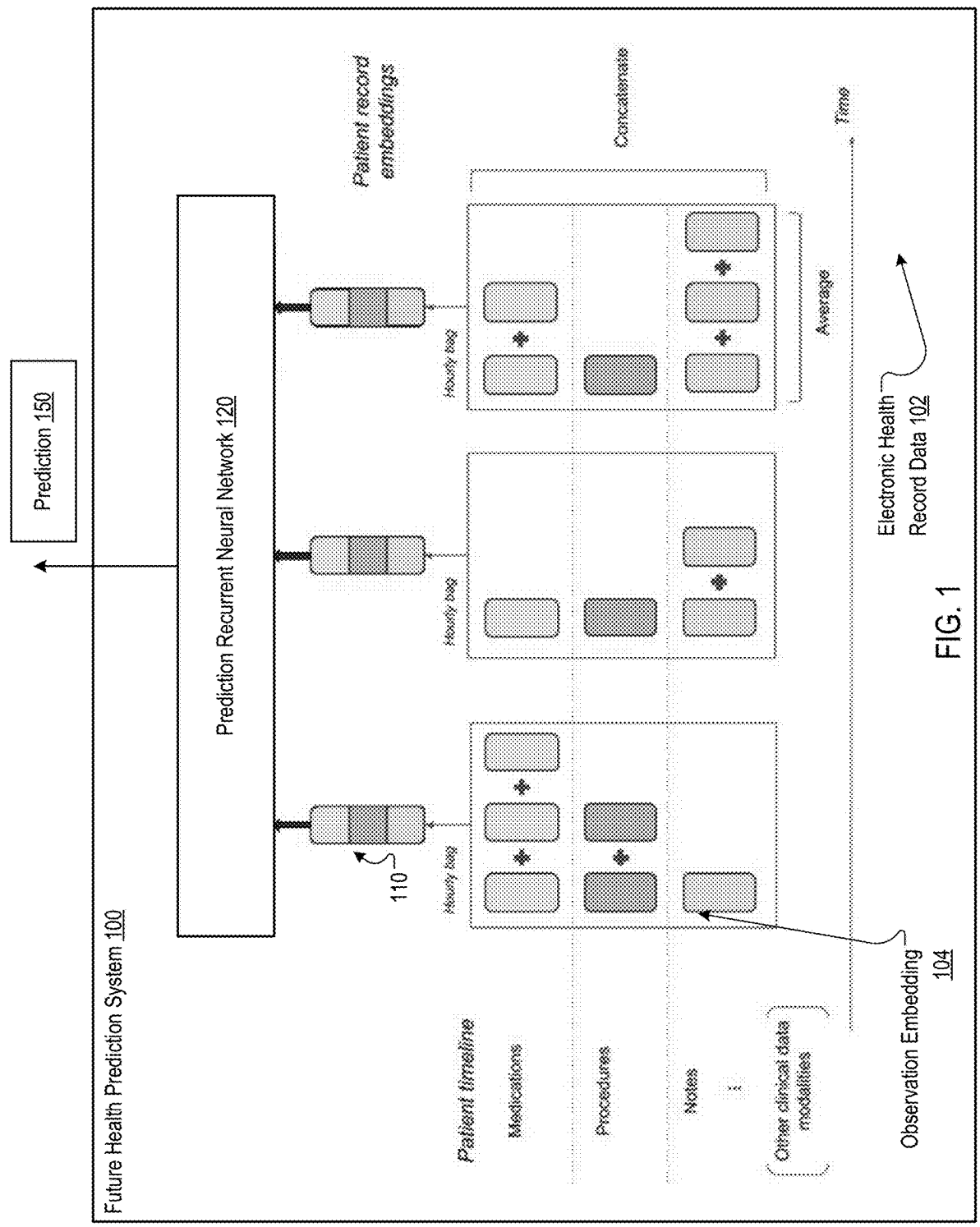
FIG. 1 shows an example future health prediction system.

FIG. 1 shows an example future health prediction system 100. The future health prediction system 100 is an example of a system implemented as computer programs on one or more computers in one or more locations in which the systems, components, and techniques described below are implemented.

The system 100 makes predictions that characterize the predicted future health of a patient. The predictions are made based on electronic health record data 102 for the patient.

The electronic health record data includes one or more observations of each of a plurality of different feature types, e.g., medications, procedures, and so on. In the example of FIG. 1, the electronic health record data includes features of the medication feature type, the procedures feature type, the clinical notes feature type, and, optionally, features gathered from other clinical data modalities.

More specifically, the plurality of different feature types includes a clinical note feature type and each observation of the clinical note feature type is a clinical note that includes a respective sequence of text tokens. Generally, clinical notes are text sequences generated by a clinician, i.e., a healthcare professional, and often include information that is relevant to the patient's current and future health. Unlike the other feature types, the clinical notes are generally raw, free text. As one example, the clinician may directly generate the text sequence by inputting text through an input modality, e.g., a keyboard or touchscreen, on a user computer. As another example, the clinician may speak the contents of the note into a microphone of the user computer and the system 100 or another system may generate the text sequence by applying automatic speech recognition to the speech of the clinician.

To generate the prediction, the system generates a respective observation embedding 104 for each of the observations and then generates an embedded representation of the electronic health record data using the observation embeddings 104. In particular, the embedded representation includes a respective patient record embedding 110 corresponding to each of a plurality of time windows and, to generate the patient record embedding 110 for a given time window, the system combines the observation embeddings of observations occurring during the time window. The set of observations occurring during a given time window is referred to in FIG. 1 as an "hourly bag," but the time window can have any appropriate length, e.g., one hour, four hours, six hours, twelve hours, or twenty-four hours. In some cases, any observations occurring more than a threshold amount of time, e.g., one thousand hours or more, before the current time are grouped into a single, "history" time window that precedes all of the other time windows in the embedded representation.

An "embedding" as used in this specification is a numeric representation in a particular space, i.e., an ordered collection of numeric values, e.g., a vector of floating point values or other type of numeric value, having a particular dimensionality.

In particular, when there are multiple observations of the same feature type occurring within a given time window, the system 100 combines the observation embeddings of that feature type, e.g., by averaging or summing the embeddings, to generate a combined observation. When only a single observation of the feature type occurs during the time window, the system 100 uses the single observation embedding of that feature type as the combined observation embedding. When no observations of a given type occur during a time window, the system 100 can include a default embedding as the combined embedding for that feature type.

The system 100 then combines, e.g., concatenates, the combined feature embeddings for the feature types to generate the patient record embedding 110 for the given time window.

The system 100 then processes the embedded representation of the electronic health record data using a prediction recurrent neural network 120 to generate a neural network output 150 that characterizes the future health status of the patient after the last time window in the embedded representation.

The prediction recurrent neural network 120 can have any recurrent neural network architecture that allows the prediction recurrent neural network 120 to map a sequence of patient record embeddings to the neural network output 150. For example, the neural network 120 can be a long short-term memory (LSTM) neural network or another type of recurrent neural network, e.g., a vanilla recurrent neural network, a gated recurrent unit neural network, and so on, with an output layer that has the appropriate number of neurons.

The future health status of the patient is the status of the patient's health with respect to one or more predetermined aspects.

As one example, the network output 150 can predict a likelihood of inpatient mortality. In other words, network output 150 can include a score that represents the likelihood of a mortality event while the patient is admitted at a medical facility.

As another example, the network output 150 can predict a discharge diagnosis at the time the patient is discharged from care, e.g., by generating a probability distribution over a set of possible diagnoses. In other words, the network output 150 can include a probability distribution over a set of possible diagnoses, with the probability for each diagnosis being the probability that the diagnosis will be a diagnosis for the patient at the time that the patient is discharged from care.

As another example, the network output 150 can predict a likelihood that a particular adverse health event occurs to the patient, e.g., an organ injury, cardiac arrest, a stroke, or mortality, within some specified time from the last time window in the health record data for the patient. In other words, the network output 150 can include a score for each of one or more adverse health events that represents a likelihood that the adverse health event occurs to the patient within some specified time from the last time window.

Because the clinical notes are text sequences of variable length, conventional systems have not been able to effectively incorporate the information in clinical notes into a framework such as the one described above.

In order to account for the variable, free form nature of clinical notes, to generate the observation embedding of a clinical note, the system processes the sequence of text tokens in the clinical note using a clinical note embedding long short-term memory (LSTM) neural network to generate a respective token embedding for each of the text tokens and generates the observation embedding for the clinical note from the token embeddings for the text tokens in the clinical note, e.g., by aggregating the token embeddings using a learned attention weighting.

This will be described in more detail below with reference to FIG. 2.

By generating the observation embeddings of the clinical note as described in this specification, the system 100 can effectively and accurately predict the risk the future health status of the patient. Accordingly, by employing the described techniques, clinicians can be provided with accurate prediction data that can then allow them to effectively treat the patient, e.g., by taking preventative action in advance of the future health actually occurring.

For observations that are of a type other than clinical notes, the system 100 can generate the observation embedding in a conventional manner. For example, to generate the observation embedding for any observations that are discrete, i.e., that can only take one or more values from a discrete set of possible values, the system 100 maps the observation to a learned embedding for the observation. As another example, to generate an observation embedding for any observations that are continuous, i.e., that are medical test results or other medical data that can take any value within some range of values, the system 100 standardizes the observation using a cohort mean and standard deviation for the feature type to generate the observation embedding. In other words, the system generates a standardized value by normalizing the continuous observation using the cohort mean and standard deviation for the feature type and then uses the standardized value as the observation embedding.

Once the neural network output 150 has been generated, the system 100 can provide the information in the network output 150 for use by a medical professional in treating the patient or store the information in the network output 150 for later access by a medical professional. As one example, the system 100 can determine whether any of the scores or probabilities in the output 150 exceed a corresponding threshold and, if so, transmit an alert for presentation to a user, e.g., to a user computer of a physician or other medical personnel.

As another example, the system 100 can generate a user interface presentation based on the data in the neural network output 150, e.g., a presentation that conveys the patient's predicted future health, and then provide the user interface presentation for display on the user computer.

In some implementations, the system 100 continually updates the neural network output 150 as new electronic health record data for the patient becomes available. For example, the system 100 can generate an initial embedded representation and generate an initial neural network output when a patient is admitted for treatment or at another initial time point. The system 100 can then obtain new data at the expiration of each subsequent time window and generate updated neural network outputs for each of the subsequent time windows until the patient is discharged or until some other termination criteria are satisfied.

Figure 2:
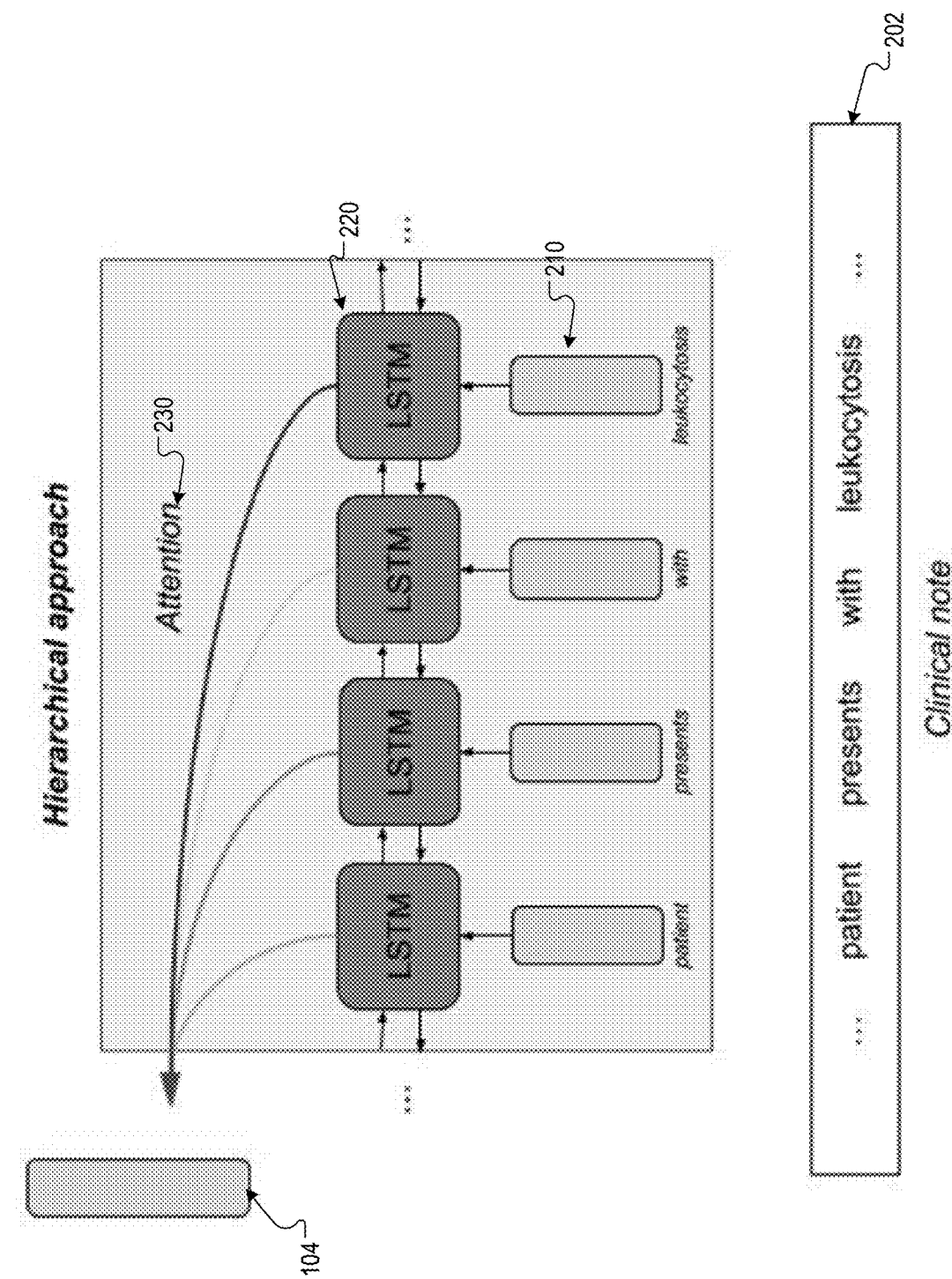
FIG. 2 shows an example of generating a clinical note embedding.

FIG. 2 shows an example of generating an observation embedding 104 for a clinical note 202.

As described above, clinical notes are text sequences generated by a clinician, i.e., a healthcare professional, and often include information that is relevant to the patient's current and future health. A text sequence is a sequence of text tokens, i.e., words or characters. Unlike the other feature types, the clinical notes are generally raw, free text. In the particular example of FIG. 2, the clinical note 202 is a text sequence that includes the fragment "patient presents with leukocytosis."

To generate the observation embedding 104 for the clinical note 202, the system processes the sequence of text tokens in the clinical note 202 using a clinical note embedding long short-term memory (LSTM) neural network 220 to generate a respective token embedding for each of the text tokens.

As part of the processing of the observation embedding 104, the neural network 220 generates an initial embedding 210 for each of the text tokens, i.e., by mapping each token to an embedding for the token using a look-up table or an embedding neural network layer. In the example of FIG. 2, the neural network 220 has generated respective initial embeddings 210 for each of the tokens "patient," "presents," "with," and "leukocytosis." These embeddings can either be learned jointly with the training of the clinical note LSTM neural network 220 or can be fixed prior to the training of the clinical note LSTM neural network 220.

In some implementations, the clinical note LSTM neural network 220 is a uni-directional LSTM neural network, i.e., an LSTM neural network that processes the text tokens in the order in which the tokens occur in the clinical note. In some other implementations, the clinical note embedding LSTM neural network is a bi-directional LSTM neural network that processes the text tokens both in a forward order, i.e., in the order in which the tokens occur in the clinical note, and in a backward order, i.e., in the opposite order from the order in which the tokens occur, to generate the respective token embeddings.

While the neural network 220 is described as being an LSTM, the neural network 220 can generally be any type of recurrent neural network, e.g., a vanilla recurrent neural network or a gated recurrent unit neural network.

Because the neural network 220 is a recurrent neural network and processes the tokens in order, the token embeddings generated by the neural network 220 are dependent on the order in which the tokens occur in the note and therefore provide a more informational representation than conventional, e.g., bag-of-words or computing statistics just from the top N most frequently occurring tokens, techniques.

The system then generates the observation embedding 104 for the clinical note 202 from the token embeddings for the text tokens in the clinical note.

In some implementations, the system combines the token embeddings in a fixed manner to generate the observation embedding 104, e.g., computes an average or other measure of central tendency of the token embeddings.

In some other implementations, like in the example of FIG. 2, the system applies a learned attention weighting 230 to the token embeddings to generate the observation embedding 104. In other words, the system aggregates the token embeddings for the text tokens in the clinical note using a learned attention weighting to generate the observation embedding 104. Generally, the learned attention weighting generates a respective weight for each token embedding that is based on one or more learned values, i.e., learned during the training of the neural network 220, and the token embeddings for the tokens in the note.

More specifically, to apply the learned attention weighting 230, the system generates a respective initial weight for each token embedding by computing a dot product between a learned context vector and the token embedding.

The system then generates a respective normalized weight for each token embedding using the initial weight for the token embedding, the learned context vector, a learned bias vector, and the initial weights for the other token embeddings. In particular, the normalized weight at for the token embedding ht can satisfy:

$$a_t = \frac{\exp(q^T h_t)}{\exp(q^T b) + \sum_{t'=1}^{T} \exp(q^T h_{t'})},$$

where q is the learned context vector, b is the learned bias vector, and T is the total number of tokens in the clinical note.

The system then computes a weighted sum of the token embeddings, with each token embedding being weighted by the corresponding normalized weight. This weighted sum can then be used as the observation embedding 104.

In order for the system to use the clinical note LSTM neural network and the prediction recurrent neural network to make accurate predictions, the system trains these two neural networks jointly on training data that includes ground truth network outputs. That is, the training data includes a set of electronic health record data, and for each electronic health record data in the set, a ground truth network output that should be generated by the prediction recurrent neural network for the electronic health record data. The system can train the neural networks jointly on this training data through supervised learning by minimizing an appropriate loss function that measures errors between the network outputs generated by the prediction neural network and the corresponding ground truth outputs, e.g., a cross-entropy loss function.

When the attention weighting 230 is used, the system can train the clinical note LSTM neural network, the prediction recurrent neural network, and the attention weighting jointly on the same training data that includes ground truth network outputs.

In some implementations, prior to this joint training, the system pre-trains the clinical note LSTM neural network using unsupervised learning on a set of training sequences extracted from training clinical notes to predict, for each training sequence, at least a next word that follows the last word in the training sequence in the training clinical note. When the clinical note LSTM is a bi-directional LSTM, the system can also train the network to predict the word that precedes the first word in the training sequence in the clinical note. This pre-training can enrich the representations generated by the clinical note LSTM and can allow the embeddings generated by this LSTM to encode a flexible, generalizable language representation of the corresponding clinical notes.

Figure 3:
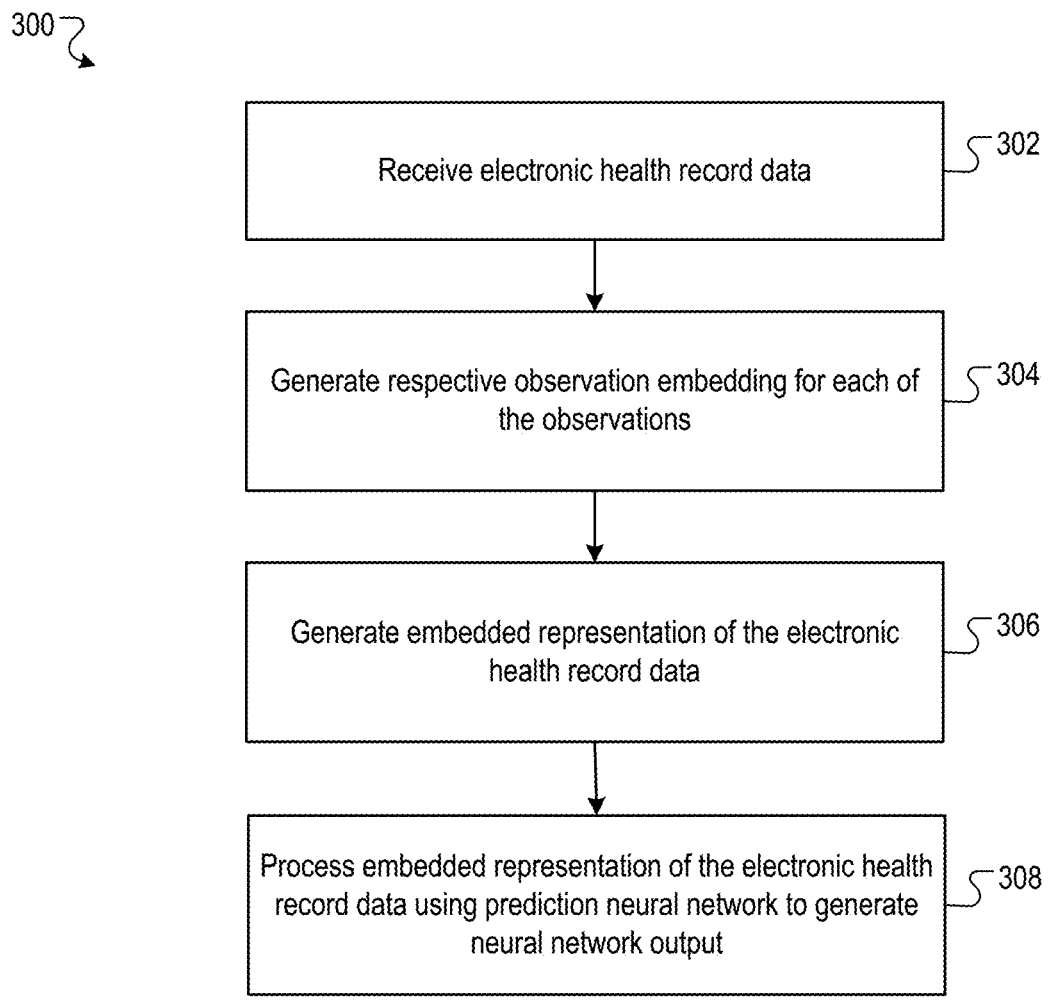
FIG. 3 is a flow diagram of an example process for generating a future health prediction.

FIG. 3 is a flow diagram of an example process 300 for generating a future health prediction. For convenience, the process 300 will be described as being performed by a system of one or more computers located in one or more locations. For example, a future health prediction system, e.g., the future health prediction system 100 of FIG. 1, appropriately programmed, can perform the process 300.

The system receives electronic health record data for a patient (step 302). The electronic health record data includes one or more observations of each of a plurality of different feature types and the plurality of different feature types includes a clinical note feature type. Each observation of the clinical note feature type is a clinical note that includes a respective sequence of text tokens.

The system generates a respective observation embedding for each of the observations (step 304). To generate the observation embedding for any observations that are clinical notes, the system processes the sequence of text tokens in the clinical note using a clinical note embedding long short-term memory (LSTM) neural network to generate a respective token embedding for each of the text tokens and generates the observation embedding for the clinical note from the token embeddings for the text tokens in the clinical note. To generate an observation embedding for any observations that are discrete, i.e., that can only take one or more values from a discrete set of possible values, the system maps the observation to a learned embedding for the observation. To generate an observation embedding for any observations that are continuous, i.e., that are diagnostic test results or other medical data that can take any value within some range of values, the system standardizes the observation using a cohort mean and standard deviation for the feature type.

The system generates an embedded representation of the electronic health record data (step 306). The embedded representation includes a respective patient record embedding corresponding to each of multiple time windows, e.g., time windows that each cover the same, fixed amount of time. Within the embedded representation, the patient record embeddings can be arranged in a sequence starting from the earliest time window.

To generate a patient record embedding for any given time window, the system combines the observation embeddings of observations occurring during the time window. In particular, for each feature type, the system can combine all of the observation embeddings of observations of the feature type that occurred during the time window to generate a combined observation embedding for the feature type and combine the combined observation embeddings to generate the patient record embedding. For example, to combine all observation embeddings of observations of the feature type that occurred during the time window, the system can average all observation embeddings of observations of the feature type that occurred during the time window. As another example, to combine the combined observation embeddings to generate the patient record embedding the system can concatenate the combined observation embeddings.

The system processes the embedded representation of the electronic health record data using a prediction recurrent neural network to generate a neural network output (step 308). Generally, the neural network output characterizes a future health status of the patient after the last time window in the embedded representation. The future health status of the patient is the status of the patient's health with respect to one or more predetermined aspects. For example, the network output can predict one or more of: a likelihood of inpatient mortality, a discharge diagnosis at the time the patient is discharged from care, a likelihood that a particular adverse health event occurs, e.g., an organ injury, cardiac arrest, a stroke, or mortality within some specified time of the last time window, and so on.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs. The one or more computer programs can comprise one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system comprising one or more computers and one or more storage devices storing instructions that, when executed by the one or more computers, cause the one or more computers to perform operations comprising:
   receiving electronic health record data for a patient,
      the electronic health record data comprising one or more observations of each of a plurality of different feature types, and
      the plurality of different feature types including a clinical note feature type, wherein each observation of the clinical note feature type is a clinical note comprising a respective sequence of text tokens;
   generating a respective observation embedding for each of the observations, comprising, for each clinical note:
      processing the sequence of text tokens in the clinical note using a clinical note embedding long short-term memory (LSTM) neural network to generate a respective token embedding for each of the text tokens; and
      generating the observation embedding for the clinical note from the token embeddings for the text tokens in the clinical note, comprising computing a weighted sum of the token embeddings, with each token embedding being weighted by a corresponding weight;
   generating an embedded representation of the electronic health record data, wherein the embedded representation comprises a respective patient record embedding corresponding to each of a plurality of time windows, and wherein generating the embedded representation comprises, for each time window:
      combining the observation embeddings of observations occurring during the time window to generate the patient record embedding corresponding to the time window; and
   processing the embedded representation of the electronic health record data using a prediction recurrent neural network to generate a neural network output that characterizes a future health status of the patient after the last time window in the embedded representation.

2. The system of claim 1, wherein combining the observation embeddings to generate the patient record embedding corresponding to the time window comprises:
   for each feature type, combining all observation embeddings of observations of the feature type that occurred during the time window to generate a combined observation embedding for the feature type; and
   combining the combined observation embeddings to generate the patient record embedding.

3. The system of claim 2, wherein combining all observation embeddings of observations of the feature type that occurred during the time window to generate a combined observation embedding for the feature type comprises averaging all observation embeddings of observations of the feature type that occurred during the time window.

4. The system of claim 2, wherein combining the combined observation embeddings to generate the patient record embedding comprises concatenating the combined observation embeddings.

5. The system of claim 1, wherein the clinical note embedding LSTM neural network is a bi-directional LSTM neural network.

6. The system of claim 1, wherein generating the observation embedding for the clinical note from the token embeddings for the text tokens in the clinical note comprises:
   aggregating the token embeddings for the text tokens in the clinical note using a learned attention weighting to generate the observation embedding.

7. The system of claim 6, wherein aggregating using the learned attention weighting comprises:
   generating a respective initial weight for each token embedding by computing a dot product between a learned context vector and the token embedding;
   generating a respective normalized weight for each token embedding using the initial weight for the token embedding, the learned context vector, a learned bias vector, and the initial weights for the other token embeddings; and
   computing the weighted sum of the token embeddings, with each token embedding being weighted by the corresponding normalized weight.

8. The system of claim 6, the operations further comprising:
   training the clinical note LSTM neural network and the prediction recurrent neural network jointly on training data including ground truth network outputs.

9. The system of claim 8, wherein training the clinical note LSTM neural network and the prediction recurrent neural network jointly on training data including ground truth network outputs comprises:
training the clinical note LSTM neural network, the prediction recurrent neural network, and the attention weighting jointly on the training data including ground truth network outputs.

10. The system of claim 8, the operations further comprising:
prior to the training, pre-training the clinical note LSTM neural network using unsupervised learning on a set of training sequences extracted from training clinical notes to predict, for each training sequence, at least a next word that follows the last word in the training sequence in the training clinical note.

11. The system of claim 1, wherein the network output comprises a prediction of inpatient mortality of the patient.

12. The system of claim 1, wherein the network output comprises a prediction of a primary diagnosis of the patient at discharge.

13. The system of claim 1, wherein the network output comprises a prediction of a set of diagnoses for the patient at discharge.

14. The system of claim 1, wherein generating a respective observation embedding for each of the observations, comprises, for each observation that is of a feature type that is discrete:
mapping the observation to a learned embedding for the observation.

15. The system of claim 1, wherein generating a respective observation embedding for each of the observations, comprises, for each observation that of a feature type that is continuous:
standardizing the observation using a cohort mean and standard deviation for the feature type.

16. One or more non-transitory computer-readable storage media storing instructions that when executed by one or more computers cause the one or more computers to perform operations comprising:
receiving electronic health record data for a patient,
the electronic health record data comprising one or more observations of each of a plurality of different feature types, and
the plurality of different feature types including a clinical note feature type, wherein each observation of the clinical note feature type is a clinical note comprising a respective sequence of text tokens;
generating a respective observation embedding for each of the observations, comprising, for each clinical note:
processing the sequence of text tokens in the clinical note using a clinical note embedding long short-term memory (LSTM) neural network to generate a respective token embedding for each of the text tokens; and
generating the observation embedding for the clinical note from the token embeddings for the text tokens in the clinical note, comprising computing a weighted sum of the token embeddings, with each token embedding being weighted by a corresponding weight;
generating an embedded representation of the electronic health record data, wherein the embedded representation comprises a respective patient record embedding corresponding to each of a plurality of time windows, and wherein generating the embedded representation comprises, for each time window:
combining the observation embeddings of observations occurring during the time window to generate the patient record embedding corresponding to the time window; and
processing the embedded representation of the electronic health record data using a prediction recurrent neural network to generate a neural network output that characterizes a future health status of the patient after the last time window in the embedded representation.

17. A computer-implemented method comprising: receiving electronic health record data for a patient,
the electronic health record data comprising one or more observations of each of a plurality of different feature types, and
the plurality of different feature types including a clinical note feature type, wherein each observation of the clinical note feature type is a clinical note comprising a respective sequence of text tokens;
generating a respective observation embedding for each of the observations, comprising, for each clinical note:
processing the sequence of text tokens in the clinical note using a clinical note embedding long short-term memory (LSTM) neural network to generate a respective token embedding for each of the text tokens; and
generating the observation embedding for the clinical note from the token embeddings for the text tokens in the clinical note, comprising computing a weighted sum of the token embeddings, with each token embedding being weighted by a corresponding weight;
generating an embedded representation of the electronic health record data, wherein the embedded representation comprises a respective patient record embedding corresponding to each of a plurality of time windows, and wherein generating the embedded representation comprises, for each time window:
combining the observation embeddings of observations occurring during the time window to generate the patient record embedding corresponding to the time window; and
processing the embedded representation of the electronic health record data using a prediction recurrent neural network to generate a neural network output that characterizes a future health status of the patient after the last time window in the embedded representation.

18. The method of claim 17, wherein combining the observation embeddings to generate the patient record embedding corresponding to the time window comprises:
for each feature type, combining all observation embeddings of observations of the feature type that occurred during the time window to generate a combined observation embedding for the feature type; and
combining the combined observation embeddings to generate the patient record embedding.

19. The method of claim 18, wherein combining all observation embeddings of observations of the feature type that occurred during the time window to generate a combined observation embedding for the feature type comprises averaging all observation embeddings of observations of the feature type that occurred during the time window.

20. The method of claim 17, wherein the clinical note embedding LSTM neural network is a bi-directional LSTM neural network.

* * * * *